United States Patent
Gupta et al.

(10) Patent No.: US 8,399,677 B2
(45) Date of Patent: Mar. 19, 2013

(54) METHOD FOR THE PREPARATION OF FENTANYL

(75) Inventors: Pradeep Kumar Gupta, Gwalior (IN); Laxmi Manral, New Delhi (IN); Kumaran Ganesan, Gwalior (IN); Ramesh Chandra Malhotra, Gwalior (IN); Krishnamurthy Sekhar, New Delhi (IN)

(73) Assignee: Defence Research & Development Organisation, Bhawan (IN)

( * ) Notice: Subject to any disclaimer, the term of this patent is extended or adjusted under 35 U.S.C. 154(b) by 156 days.

(21) Appl. No.: 12/922,906

(22) PCT Filed: Mar. 9, 2009

(86) PCT No.: PCT/IN2009/000159
§ 371 (c)(1),
(2), (4) Date: Sep. 16, 2010

(87) PCT Pub. No.: WO2009/116084
PCT Pub. Date: Sep. 24, 2009

(65) Prior Publication Data
US 2011/0021781 A1      Jan. 27, 2011

(30) Foreign Application Priority Data

Mar. 19, 2008   (IN) .............................. 696/DEL/2008

(51) Int. Cl.
*C07D 211/56* (2006.01)
(52) U.S. Cl. ........................................ 546/224; 514/317
(58) Field of Classification Search .................. 514/317; 546/224
See application file for complete search history.

(56) References Cited

U.S. PATENT DOCUMENTS 3,164,600  A        1/1965   Janssen
4,197,303  A  *   4/1980   Sanczuk et al. ............... 514/329

OTHER PUBLICATIONS

Siegfried "Synthesis of fentanyl" Rhodium Chemistry Archive p. 1-3 (2005).*
Seddon "Pseudopolymorph . . . " Crystal groth & design 4(6) 1087 (2004).*
Braga et al. "Making crystals from crystals . . . " J. Roy. Soc. Chem. Chemm, Commu. p. 3635-3645 (2005).*
Micovic et al., 3-Carbomethoxy Fentanyl: Synthesis, Pharmacology, and Conformational Analysis, Heterocyclic Communications, 1998, vol. 4, pp. 171-179, also pp. 172-173.
Ivanovic et al., The Synthesis and Pharmacological Evaluations of 2, 3-seco-fentanyl analogues, Journal of Serbian Chemistry Society, 2004, vol. 69, pp. 955-968.
Micovic et al., The Synthesis and Preliminary Pharmaological Evaluation of 4-Methyl Fentanyl, Biorganic and Medicinal Chemistry Letter 2000, vol. 10, pp. 2011-2014.

* cited by examiner

*Primary Examiner* — Celia Chang
(74) *Attorney, Agent, or Firm* — The Webb Law Firm

(57) ABSTRACT

The invention provides a method for the preparation of fentanyl comprising: (a) reacting 4-piperidone hydrochloride monohydrate with aniline in presence of reducing environment to produce 4-anilinopiperidine (4-AP), (b) reacting the 4-AP as obtained from step (a) with phenethyl halide under reflux conditions in highly alkaline medium to give 4-anilino-N-phenethylpiperidine, and (c) converting the 4-anilino-N-phenethylpiperidine to fentanyl by reacting with propionyl chloride in presence of halogenated hydrocarbons, then isolating fentanyl by solvent extraction and purifying by crystallization from petroleum ether at a temperature ranging from 60-80° C.

11 Claims, No Drawings

METHOD FOR THE PREPARATION OF FENTANYL

CROSS REFERENCE TO RELATED APPLICATIONS

This application is a United States Application under 35 U.S.C. 371 claiming benefit of PCT Application No. PCT/IN2009/000159, filed on Mar. 9, 2009, which claims the benefit of Indian Patent Application No. 696/DEL/2008, filed on Mar. 19, 2008, the contents of each of which are incorporated herein by reference.

FIELD OF THE INVENTION

This invention particularly relates to a method that is simple, high yielding, cost effective, eco-friendly, environmentally safe, industrially feasible, does not require stringent process conditions, sophisticated infrastructure and specially skilled personnel.

BACKGROUND OF THE INVENTION

Fentanyl is a synthetic m-opioid receptor agonist with high lipid solubility. Fentanyl is generic name given to the chemical compound N-(1-phenethyl-4-piperidyl)propionanilide. It is well known narcotic analgesic used for both general as well as regional anesthesia and both during and or after surgery. It is 30 to 100 times more powerful than morphine and shows less emetic activity than morphine. Fentanyl citrate was first used as an intravenous anesthetic under the name 'Sublimaze' in 1960. It is also mydritic and cholinergic in its action and found useful as analgesic particularly treating cancer pain. It has an analgesic potency 1000 times that of morphine. It has more than 12 different analogs.

Fentanyl was first synthesized in 1960 by Paul Janssen founder of Janssen Pharmaceutica involving reacting N-phenethylpiperidone with aniline to produce 4-anilino-N-phenethylpiperidone with yield of about 50-80% using sodium borohydride at room temperature followed by reacting with propionyl chloride in presence of pyridine wherein the reaction is exothermic and thus requires stringent process conditions. The fentanyl thus obtained with a yield over 90% is further purified by crystallization.

U.S. Pat. No. 3,164,600 ('600) dated Jan. 5, 1965 to Janssen in column 2 lines 45 to 70 and column 3, (Examples), discloses a process for the preparation of fentanyl that involves following five steps:
(i) refluxing mixture of 1-benzyl-4-piperidone, aniline, toluene and 4 toluenesulfonic acid for 15 hrs to produce N-(1-benzyl-4-piperydylidene)aniline,
(ii) reducing N-(1-benzyl-4-piperydylidene)aniline so obtained using lithium aluminium hydride in anhydrous ether to 1-benzyl-4-anilinopiperidine in nitrogen atmosphere, then
(iii) alkalizing by refluxing with propionic anhydride for 7 hrs to give N-(1-benzyl-4-piperydylidene)propionanilide,
(iv) subjecting to debenzylation by employing hydrogenation over palladium on charcoal catalyst in ethanol to get N-(4-piperydyl)propionanilide, and finally
(v) treating a mixture of N-(4-piperydyl)propionanilide, sodium carbonate and potassium iodide in hexone with the solution of β phenethylchloride in 4-methyl-2-pentanone and refluxed for 27 hrs to obtain fentanyl [N-(1-phenethyl-4-piperidyl)propionanilide].

The main disadvantage associated with this process is a multi-step, hence requires more time and over all appreciably reduced yield.

The other drawback is that it requires stringent operating conditions such as reflux temperature in all five steps thus making the process energy extensive, which in turn makes the process uneconomical.

The other drawback is that every process step makes use of organic solvent requiring removal of these solvents, which not only adds to the overall cost of the process but also makes the process environmentally unsound and unsafe.

Further steps (i), (ii), (iii), & (v) being moisture sensitive requires additional infrastructure and precautions, which is undesirable for large scale production.

Lithium aluminium hydride in step (ii) reacts violently with water and liberates hydrogen, which is likely to cause the material ignite. Thus, for large scale production, use of lithium aluminium hydride in step (ii) is undesirable from safety and environmental point of view.

Additionally, the diethyl ether used is highly inflammable low boiling organic solvent posing fire hazards that requires special fire safety measures particularly in up scaling of the process.

Similarly the palladium charcoal used in hydrogenation/debenzylation increases the cost of the process.

Further, the effluent stream of the subject process is likely to impair the environment.

In general, the process as disclosed in '600 is energy extensive, cost extensive, time consuming, requires sophisticated infrastructure to maintain stringent operating conditions, requires specially trained skilled personnel, likely to impair ecosystem & environment and unfit for large scale production, i.e., industrially and commercially unviable.

Polish patent No. 72,416 describes a process for the preparation of fentanyl also comprises of following five steps:
(i) condensation of 2-phenylethylamine with methyl or ethyl acrylate to get N,N-bis(2carbalkoxyethyl)-phenylethylamine,
(ii) cyclising the said amine in presence of sodium methoxide (alkoxide) to give 1-(2-phenylethyl)piperidine-4-one,
(iii) condensing the said 1-(2-phenylethyl)piperidine-4-one with aniline to give 1-(2-phenylethyl)piperidinylidene aniline, followed by
(iv) reducing by employing lithium aluminium hydride and subsequently
(v) acylating to procure fentanyl.

One of the main drawbacks associated with this process is employing moisture sensitive sodium methoxide and lithium aluminium hydride, the threats of which are described herein before.

Further, this process also involves five steps and thus inherits the draw backs associated therewith.

In general, this process is also cost extensive, unsafe to environment, requires special operational conditions and thus unfeasible for industrial and commercial applications.

The Indian application No. 2554/DEL/2004 to DRDO discloses a method comprising: (i) refluxing 4-piperidonehydrochloride monohydrate with phenethyl bromide in acetonitrile in presence of potassium carbonate and Tetra butyl Ammonium Bromide (TABA) to give NPP (N-phenethyl-4-piperidone) (II) reacting NPP with aniline in presence of zinc and carboxylic acid preferably acetic acid to give ANPP, then reacting with propionyl chloride to get fentanyl. This process claims advantage over the prior art in (a) reducing number of steps from five to 3, (b) employing all readily available indigenously available reactants, and (c) eliminating employing moisture sensitive (sodium methoxide), fire hazard reagents (lithium metal hydride) and highly flammable low boiling solvent.

Though the process disclosed in the application is obviating drawbacks of the existing process to some extent, it suffers from the following drawbacks:

The process is low yielding,

Polymerization of 4-piperidone hydrochloride monohydrate reactant takes place in step (i), which results in increased load on effluent, Using organic solvent as a reaction medium and removal of organic solvent is necessary; this adds to the cost as well as makes the process environmentally unsafe/unsound.

Requirement of anhydrous conditions.

In view of this there is a need to provide simple, high yielding, cost effective, eco-friendly, environmentally safe, sound and beneficial, industrially feasible, that does not require stringent process conditions, sophisticated infrastructure and especially skilled personnel.

OBJECTIVE OF THE INVENTION

The main object of this invention is to provide a method for the preparation of fentanyl obviating the draw backs of the existing processes.

The other object of this invention is to provide a process having yield more than 60%.

Another object of this invention is to provide a process that does not require organic solvent as the reaction medium thereby making the process cost effective as well as eco-friendly.

Yet other object of this invention is to provide a process that avoids using hazardous reagents such as herein before disclosed, thereby making the process environmentally safe, sound and beneficial.

Yet another object of this invention is to provide an energy efficient process by reducing number of steps involved.

Still another object of this invention is to provide a process that does not require purification of intermediate.

Yet another objective is to provide a process wherein polymerization of the starting material is avoided, thereby reducing the effluent load and making the process environment friendly environmentally sound and beneficial.

The novelty of the present invention resides in eliminating hazardous reagent such as sodium borohydrate, sodium methoxide, lithium aluminium hydride, ether; using different starting material, avoiding polymerization of reagents, directing process in predetermined manner, and eliminating using organic solvents.

Accordingly, the process of the present invention though uses N-phenethylpiperidone as one of the starting materials as disclosed by Janssen in 1960, but differs from his process in avoiding employing sodium borohydride and eliminating exothermic reactions. This results in making process economical and environmentally safe.

The process of the present invention employs 4-piperidone hydrochloride monohydrate as starting material as against benzyl protected benzyl-4-piperidone being used in '600. Additionally, the hazardous reagents such as lithium aluminium hydride, inflammable low boiling solvents, high cost reagents such palladium charcoal and stringent process conditions being used in '600 are totally eliminated in the process of the subject application. Liberation of H ion required for reduction of imine formed through reaction of the starting material and aninline is regulated by avoiding escape of H from the reaction mass by replacing toluene and para toluene sulfonic acid (PTSA) by metal and aqueous carboxylic acid.

The process also differs from the one disclosed in Polish Patent as mentioned herein above, in not using sodium methoxide and lithium aluminium hydride in addition to reducing the number of steps from five to three.

The process of the present invention also has technical advancement over the Indian application No. 2554/DEL/2004. 4-piperidone hydrochloride monohydrate when reacts with potassium carbonate gets converted to free base and in this condition the amino and carbonyl groups of the reactant react and form polymer increasing load on effluent. Though the number of steps are three and starting material 4-piperidone hydrochloride monohydrate is same in both these processes, the process of the present invention gives solution to overcoming polymerization of 4-piperidone hydrochloride monohydrate and proving the process environmentally sound, which is one of the major influencing factors. Additionally, elimination of organic solvents by aqueous medium reduces the cost of present invention substantially. The process of the present invention has overall cost reduction to the tune of 50%.

SUMMARY OF THE INVENTION

Accordingly, the present invention provides a method for the preparation of fentanyl comprising:
(a) reacting 4-piperidone hydrochloride monohydrate with aniline in presence of reducing environment to produce 4-anilinopiperidine (4-AP),
(b) alkylating/reacting the 4-AP as obtained from step (a) with phenethyl halide under reflux conditions in highly alkaline medium to give 4-anilino-N-phenethylpiperidine, and
(c) converting the said 4-anilino-N-phenethylpiperidine to fentanyl by reacting with propionyl chloride in presence of halogenated hydrocarbons then isolating fentanyl by solvent extraction and purifying by crystallization from petroleum ether (60-80° C.).

One of the embodiments of the present invention that the reducing environment comprises metal and aqueous carboxylic acid, preferably zinc or magnesium and aqueous acetic acid, more preferably, zinc and 80 to 90% acetic acid.

According to other embodiment of this invention, the reaction in step (a) may initially be conducted at room temperature for 15 to 35 hrs, preferably for 20 to 30 hrs, followed by at an elevated temperature ranging from 50 to 90° C., preferably at 65 to 80° C. for 15 to 35 hrs, preferably for 20 to 30 hrs.

According to another embodiment of this invention, in the reaction of step (a), 4-piperidone hydrochloride monohydrate and aniline may be used in 1:1 ratio.

According to yet another embodiment of this invention, the reaction in step (a) is quenched with water, preferably ice cold water, and 4-AP may be isolated by filtration followed by alkali neutralization.

According to yet another embodiment of this invention, in the reaction of step (b), the phenethyl halide used may be chloride, bromide or iodide, preferably bromide.

According to yet another embodiment of this invention, in the reaction of step (b), the highly alkaline medium may have a pH above 14 and is provided by alkali metal hydroxide preferably sodium hydroxide.

According to yet another embodiment of this invention, the reaction in step (b) may be proceeded by optionally purifying 4-AP.

According to still another embodiment of this invention, in the reaction of step (c), the halogenated hydrocarbons employed may be such as chloroform, dichloromethane, dichloroethane, tetrachloroethane, preferably dichloroethane.

According to yet another embodiment of this invention, in the reaction of step (c), 4 to 5 times propionyl chloride with respect to 4-anilino-N-phenethylpiperidine may be employed and added drop wise.

According to yet another embodiment of this invention, in the reaction of step (c), the solvent employed for solvent extraction may be halogenated hydrocarbons, preferably dichloromethane.

DETAILED DESCRIPTION

The examples provided in the detailed description are merely examples, which should not be used to limit the scope of the claims in any claim construction or interpretation.

Step I: Preparation of 4-anilinopiperidine:

To a mixture of 0.5 to 5.0 parts (w/w) of 4-piperidone hydrochloride monohydrate, preferably 1.00 to 3.00 parts (w/w) and 0.5 to 5.0 parts (w/w) of aniline, preferably 1.0 to 2.0 parts (w/w), 1 to 20 parts (w/w) of zinc preferably 4 to 12 parts (w/w) and 5 to 100 parts (w/w) of 90% acetic acid preferably 20 to 50 parts (w/w) were added and stirred at room temperature for 15 to 35 hrs, preferably 20 to 30 hrs, and then at 50 to 90° C., preferably at 65 to 80° C. for 15 to 35 hrs, preferably 20 to 30 hrs. After completion of the reaction, water was added to the reaction mixture and filtered. Crushed ice was added to the filtrate and was neutralized with excess of aqueous sodium hydroxide solution. The crude 4-anilinopiperidine was obtained by filtration. It was then recrystallized with acetone to give colorless needles of 4-anilinopiperidine, mp 105-06° C.

Step II: Preparation of 4-anilino-N-phenethylpiperidine:

In a round bottom flask, 1 to 5 parts (w/w) of 4-anilonopiperidine preferably 2 to 3 parts (w/w) prepared in step 1, 0.5 to 2.00 parts (w/w) of 100% aqueous sodium hydroxide solution preferably 1 to 3 parts (w/w) and 2 to 10 parts (w/w) of 2-phenethylbromide, preferably 4 to 6 parts (w/w) were taken. The reaction mixture was heated with stirring at 80 to 150° C. preferably at 100 to 130° C. for 2 to 10 hrs preferably 3 to 7 hrs. The reaction mixture was then poured in the ice cooled water and crude product 4-anilinophenethylpiperidine was obtained by filtration. The crude product was recrystallized with chloroform-petroleum ether (40-60° C.) to give 4-anilino-N-phenethyl-piperidine, mp 98-100° C.

Step III: Preparation of fentanyl (N-(1-phenethyl-4-piperidyl)propionanilide):

A solution of 5.5 parts (w/w) of 4-anilino-N-phenethyl-piperidine preferably 1 to 3 parts in 5 to 15 parts (w/w) of dichloroethane preferably 8 to 12 parts was taken in a two neck round bottom flask fitted with a reflux condenser, pressure equalizing funnel and calcium chloride guard tube. To this stirred solution, 2 to 20 parts 9 w/w) of propionyl chloride preferably 5 to 15 parts was added drop wise through pressure equalizing funnel. After 2 to 6 hrs, preferably 4 to 5 hrs stirring at room temperature, the reaction mixture was washed with 20% sodium hydroxide solution. The washings were extracted with 2×50 parts, preferably 65 to 70 parts dichloroethane. The combined organic phase was dried over sodium sulphate and concentrated to give fentanyl. The crude compound was recrystallised from petroleum ether (60 to 80° C.) to give colourless crystals of pure fentanyl having mp 82 to 83° C.

EXAMPLE 1

In a three neck round bottom flask equipped with mechanical stirrer and water condenser, 15.36 gm (0.10 moles) of 4-piperidone hydrochloride monohydrate and 20.95 gm (0.255 moles) of aniline was added. To this mixture, 26.14 gm (0.40 moles) of zinc and 120 gm (2.00 moles) of 90% acetic acid were added. The reaction mixture was stirred at room temperature for 12 hrs and at 50 to 70° C. for 12 hrs. Water was then added to the reaction mixture and filtered. Crushed ice was added to the filtrate and was neutralized with excess of aqueous sodium hydroxide solution. The crude 4-anilinopiperidine was obtained by filtration.

In two neck round bottom flask equipped with condenser, 17.6 gms (0.10 moles) of 4-anilinopiperidine obtained from step 1, and 50 ml of 100% sodium hydroxide was added. The reaction mixture was heated up to 120° C. and 37 gms (0.2 moles) of 2-phenethyl bromide were then added. The reaction mixture was stirred for 2 hrs. After the completion of the reaction, the reaction mixture was poured in the ice cooled water. The crude product was obtained by filtration and recrystallised from petroleum ether (60 to 80° C.) to give colourless crystals of 4-anilino-N-phenethyl piperidipure fentanyl N-(1-phenethyl-4-piperidyl)propionanilide).

In two neck round bottom flask equipped with condenser pressure equalizing funnel and calcium chloride guard tube, a solution of 28.0 (0.10 moles) of 4-anilino N-phenethyl piperidine prepared in step II, in 55 ml of dichloroethane was taken. To this solution, 9.25 gm (0.10 moles) of propionyl chloride was added drop wise through pressure equalizing funnel with continuous stirring. After the completion of the addition, the mixture was further stirred for 5 hrs. After the completion of the reaction, the reaction mixture was washed with 20% sodium hydroxide solution. The aqueous phase was extracted with 2×50 ml of dichloromethane The combined organic extract was dried over sodium sulphate and concentrated to give crude fentanyl. The crude product was recrystallised from petroleum ether (60 to 80° C.) to give colourless crystals of pure fentanyl having mp 82 to 83° C.

EXAMPLE 2

In a three neck round bottom flask equipped with mechanical stirrer and water condenser, 15.36 gm (o.10 moles) of 4-piperidone hydrochloride monohydrate and 9.3 gm (0.10 moles) of aniline were added. To this mixture, 6.5 gm (0.10 moles) of zinc and 0.6 gm (0.10 moles) of 90% acetic acid were added. The reaction mixture was stirred at room temperature for 24 hrs and at 50 to 70° C. for 24 hrs. Water was then added to the reaction mixture and filtered. Crushed ice was added to the filtrate and was neutralized with excess of aqueous sodium hydroxide solution. The crude 4-anilinopiperidine was obtained by filtration.

In two neck round bottom flask equipped with condenser 17.6 gms (0.10 moles) of 4-anilinopiperidine obtained from step 1, and 100 ml of 100% sodium hydroxide were added. The reaction mixture was heated up to 140° C. and 18.5 gms (0.1 moles) of 2-phenethyl bromide was then added. The reaction mixture was stirred for 4 hrs. After the completion of the reaction, the reaction mixture was poured in the ice cooled water. The crude product was obtained by filtration and recrystallised from petroleum ether (60 to 80° C.) to give colourless crystals of 4-anilino-N-phenethyl piperidipure fentanyl N-(1-phenethyl-4-piperidyl)propionanilide).

In two neck round bottom flask equipped with condenser pressure equalizing funnel and calcium chloride guard tube, a solution of 28.0 (0.10 moles) of 4-anilino N-phenethyl piperidine prepared in step II, in 100 ml of dichloroethane was taken. To this solution, 18.5 gm (0.20 moles) of propionyl chloride was added drop wise through pressure equalizing funnel with continuous stirring. After the completion of the addition, the mixture was further stirred for 1 hrs. After the completion of the reaction, the reaction mixture was washed with 20% sodium hydroxide solution. The aqueous phase was extracted with 2×100 ml of dichloromethane. The combined organic extract was dried over sodium sulphate and concentrated to give crude fentanyl. The crude product was recrystallised from petroleum ether (60 to 80° C.) to give colourless crystals of pure fentanyl having nip 82 to 83° C.

EXAMPLE 3

In a three neck round bottom flask equipped with mechanical stirrer and water condenser, 15.36 gm (0.10 moles) of 4-piperidone hydrochloride monohydrate and 16.43 gm (0.2 moles) of aniline were added. To this mixture, 130 gm (2.0 moles) of zinc and 120 gm (2.00 moles) of 90% acetic acid were added. The reaction mixture was stirred at room temperature for 24 hrs and at 50 to 70° C. for 24 hrs. Water was then added to the reaction mixture and filtered. Crushed ice was added to the filtrate and was neutralized with excess of aqueous sodium hydroxide solution. The crude 4-anilinopiperidine was obtained by filtration.

In two neck round bottom flask equipped with condenser 17.6 gms (0.10 moles) of 4-anilinopiperidine obtained from step 1, and 50 ml of 100% sodium hydroxide was added. The reaction mixture was heated up to 60° C. and 27.75 gms (0.15 moles) of 2-phenethyl bromide was then added. The reaction mixture was stirred for 5 hrs. After the completion of the reaction, the reaction mixture was poured in the ice cooled water. The crude product was obtained by filtration and recrystallised from petroleum ether (60 to 80° C.) to give colourless crystals of 4-anilino-N-phenethyl piperidipure fentanyl N-(1-phenethyl-4-piperidyl)propionanilide).

In two neck round bottom flask equipped with condenser pressure equalizing funnel and calcium chloride guard tube, a solution of 28.0 (0.10 moles) of 4-anilino N-phenethyl piperidine prepared in step II, in 150 ml of dichloroethane was taken. To this solution, 9.25 gm (0.10 moles) of propionyl chloride was added drop wise through pressure equalizing funnel with continuous stirring. After the completion of the addition, the mixture was further stirred for 10 hrs. After the completion of the reaction, the reaction mixture was washed with 20% sodium hydroxide solution. The aqueous phase was extracted with 2×100 ml of dichloromethane. The combined organic extract was dried over sodium sulphate and concentrated to give crude fentanyl. The crude product was recrystallised from petroleum ether (60 to 80° C.) to give colourless crystals of pure fentanyl having mp 82 to 83° C.

Alternative combinations and variations of the examples provided will become apparent based on this disclosure. It is not possible to provide specific examples for all of the many possible combinations and variations of the embodiments described, but such combinations and variations may be claims that eventually issue.

We claim:

1. A method for the preparation of fentanyl comprising: (a) reacting 4-piperidone hydrochloride monohydrate with aniline in presence of zinc and 90% acetic acid to produce 4-anilinopiperidine (4-AP), (b) reacting the 4-AP as obtained from step (a) with 2 phenethyl bromide in the presence of aqueous alkali metal hydroxide solution to give 4-anilino-N-phenethylpiperidine, and (c) preparing fentanyl by treating 4-anilino-N-phenethylpiperidine prepared in step (b) with propionyl chloride in dichloroethane.

2. The method as claimed in claim 1, wherein the reaction in step (a) is initially conducted at room temperature for 15 to 35 hrs, followed by an elevated temperature ranging from 50 to 90° C., for 15 to 35 hrs.

3. The method as claimed in claim 1, wherein in the reaction of step (a), reacting 4-piperidone hydrochloride monohydrate and aniline is used in a 1:1 ratio.

4. The method as claimed in claim 1, wherein the reaction in step (a) is quenched with water, preferably ice cold water, and the 4-AP is isolated by filtration followed by alkali neutralization.

5. The method as claimed in claim 1, wherein the reaction in step (b) is proceeded by optionally purifying the 4-AP.

6. The method as claimed in claim 1, wherein in the reaction of step (c), 4 to 5 times propionyl chloride with respect to 4-anilino-N-phenethylpiperidine is employed and added drop wise.

7. The method as claimed in claim 2, wherein the reaction in step (a) is initially conducted at room temperature for 20 to 30 hrs.

8. The method as claimed in claim 2, wherein the elevated temperature ranges from 65 to 80° C.

9. The method as claimed in claim 2, wherein the elevated temperature is maintained for 20 to 30 hrs.

10. A process for the preparation of 4-anilinopiperidine (4-AP) comprising reacting 4-piperidone hydrochloride monohydrate with aniline in the presence of zinc and 90% acetic acid.

11. A process for the preparation of 4-anilino-N-phenethylpiperidine (ANPP) comprising reacting 4-anilinopiperidine (4-AP) with 2-phenethylbromide in the presence of aqueous alkali metal hydroxide solution.

* * * * *

UNITED STATES PATENT AND TRADEMARK OFFICE
CERTIFICATE OF CORRECTION

| | | |
|---|---|---|
| PATENT NO. | : 8,399,677 B2 | Page 1 of 1 |
| APPLICATION NO. | : 12/922906 | |
| DATED | : March 19, 2013 | |
| INVENTOR(S) | : Pradeep Kumar Gupta et al. | |

It is certified that error appears in the above-identified patent and that said Letters Patent is hereby corrected as shown below:

Title Page, item (56); Column 2, OTHER PUBLICATIONS, Line 3, delete "groth" and insert -- growth --

Title Page, item (56); Column 2, OTHER PUBLICATIONS, Line 13, delete "Pharmaological" and insert -- Pharmacological --

Title Page, item (56); Column 2, OTHER PUBLICATIONS, Line 14, delete "Biorganic" and insert -- Bioorganic --

In the Claims:
Column 8, Line 11, Claim 1, delete "2 phenethyl" and insert -- 2-phenethyl --

Signed and Sealed this
Second Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO.        : 8,399,677 B2
APPLICATION NO.   : 12/922906
DATED             : March 19, 2013
INVENTOR(S)       : Gupta et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 155 days.

Signed and Sealed this
First Day of September, 2015

Michelle K. Lee
*Director of the United States Patent and Trademark Office*